United States Patent [19]

Schulman et al.

[11] 3,950,086

[45] Apr. 13, 1976

[54] DENTAL LIGHT REFLECTOR AND VISUAL-AUDIO ANALGESIC ASSEMBLY

[76] Inventors: Herbert Schulman, 24 Clematis St.; Francis P. Russo, 193 Norwood Ave.; James W. Carter, 32 Clematis St.; John L. Parry, 112 Alden Drive, all of Port Jefferson Station, N.Y. 11776

[22] Filed: Jan. 22, 1975

[21] Appl. No.: 543,168

[52] U.S. Cl. .................. 353/74; 32/22; 128/1 C; 240/2 L; 240/41.15; 352/243; 353/119; 353/122
[51] Int. Cl.² G03B 21/22; A61C 19/02; A61B 1/06
[58] Field of Search ............ 240/41.15, 2 L; 353/29, 353/74, 79, 122, 119; 128/1 C; 32/22; 352/243, 72

[56] References Cited
UNITED STATES PATENTS

| | | | |
|---|---|---|---|
| 2,798,938 | 7/1957 | Jewell | 240/41.15 |
| 3,207,847 | 9/1965 | Epstein | 128/1 C |
| 3,415,571 | 12/1968 | Heimert | 32/22 |
| 3,817,607 | 6/1974 | Anderson | 352/72 |

Primary Examiner—Houston S. Bell, Jr.
Assistant Examiner—Steven L. Stephan
Attorney, Agent, or Firm—Albert J. Santorelli

[57] ABSTRACT

A dental light reflector and visual-audio analgesic assembly having a housing including a display screen upon which a selected film is projected and/or displayed. A reflector device is mounted below the housing, and includes a reflector and interacting lamp to illuminate the area of the patient's mouth under operation by the dentist or dental assistant. The positioning of the reflector assembly with respect to the housing during normal dental procedures is such that the display screen is placed into the direct field of view of the patient without any light interference from the reflector. The film being displayed may include a soundtrack and earphones enabling the patient to listen to the soundtrack of the film. Storage means are provided along the top plate of the housing to store films for selection by the patient. The assembly including the housing and reflector device are mounted to a yoke which is transportable within a track for proper positioning of the assembly with respect to a patient seated in a dental chair.

3 Claims, 3 Drawing Figures

DENTAL LIGHT REFLECTOR AND VISUAL-AUDIO ANALGESIC ASSEMBLY

BACKGROUND OF THE INVENTION

1. Field of the Invention

The invention relates to the dental field, and particularly the use of a visual-audio analgesic and light reflector assembly to illuminate the area of the patient's mouth under operation without interfering with patient's view of a display screen.

2. Description of the Prior Art

The prior art discloses dental lighting structures supported by an overhanging swivel member. Thus for example note U.S. Pat. No. 3,191,023 which discloses a dental lighting structure.

SUMMARY OF THE INVENTION

The present invention relates to an improvement over the prior art and includes an assembly with a housing having a display screen at the front face and a reflector assembly mounted to the base portion thereof. The assembly is transportable within track means and includes mounting means to enable proper positioning relative to a seated patient. Projection means are included within the housing to project a selected film onto the display screen. The film may also comprise a soundtrack, and earphones are provided for use by the patient in order to reproduce the soundtrack.

The reflector assembly includes a reflector and lamp positioned with respect to the display screen such that it illuminates the area of the patient's mouth under operation without interfering with the patient's view of the display screen. The housing may also include storage means to store a plurality of selected films, cards and/or tapes. Control means are included to enable control of the visual and audio reproduction systems by the patient, as well as the dentist or dental assistant.

DETAILED DESCRIPTION OF THE INVENTION

Figure 1:
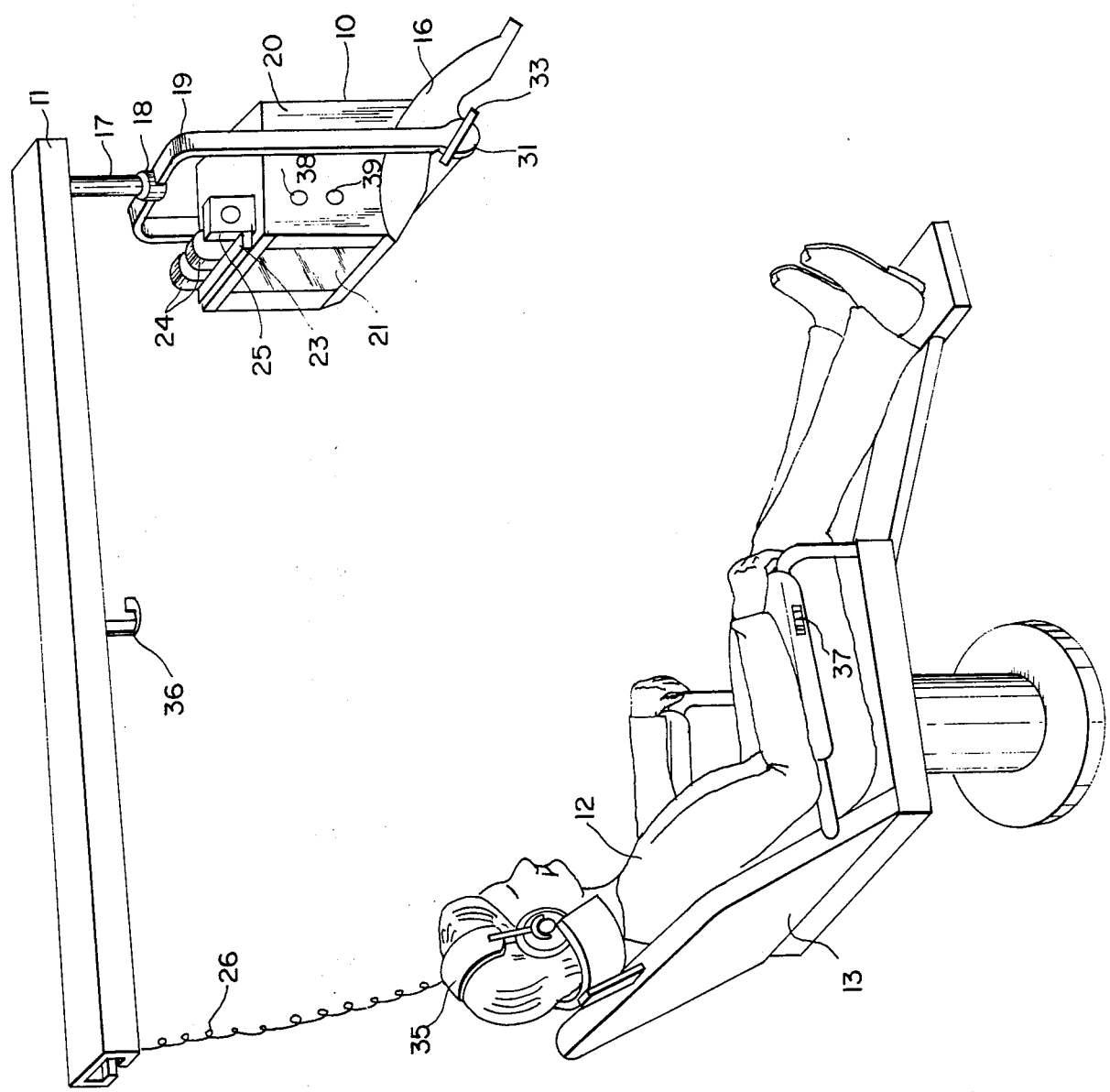
FIG. 1 is an isometric view of the visual-audio analgesic and reflector assembly according to the invention in a dental office environment.
Figure 1:
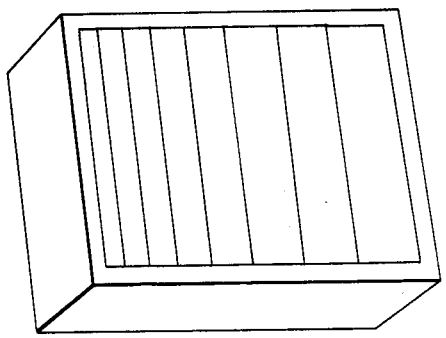

FIG. 1 shows in a dental office environment the use of the visual-audio analgesic and reflector assembly to the invention. The device is generally indicated by designation numeral 10 and is mounted within track 11 for translational movement therealong for proper positioning with respect to the patient 12. Conventional dental chair 13 is provided upon which the patient sits and assembly 10 is then pulled along track 11 by the dentist or dental assistant for positioning with respect to the patient. As shown in greater detail in FIGS. 2 and 3, assembly 10 is mounted within track 11 by means of crossbar 14 having rollers 15 and 16 for easy sliding within track 11. Support bar 17 is securely attached to mounting swivel means 18, the latter having yoke 19 passing therethrough.

The specific structure of the assembly includes housing 20, the front face of which includes display screen 21. The top plate 22 of housing 20 includes storage rack 23 mounted thereto upon which a plurality of movie film cassettes 24 are positioned for easy access to the dentist or dental assistant. Alternatively, video cards or tapes may be substituted for cassettes 24. This enables the patient to select the program he desires to view. When the program is selected by the patient, it is positioned within the playback device 25 by the dentist or dental assistant for projection and display on the screen 21.

In this respect, playback device 25 is conventional in the art and includes means to automatically thread the film, or introduce the video card or tape into the projection unit (not shown) which is included within housing 20. A conventional television receiver may be used and adapted to include a system to play back magnetic video cards and/or tapes. The particular projection unit is conventional in the art and is not described in detail herein. The film or magnetic video card and/or tape may include a soundtrack correlated thereto which may be reproduced for hearing by the patient through earphones 35. The electrical wiring for the electrical signals produced from the soundtrack by reproduction means which may be included within housing 20 (not shown) is shown by wire 26.

Figure 3:
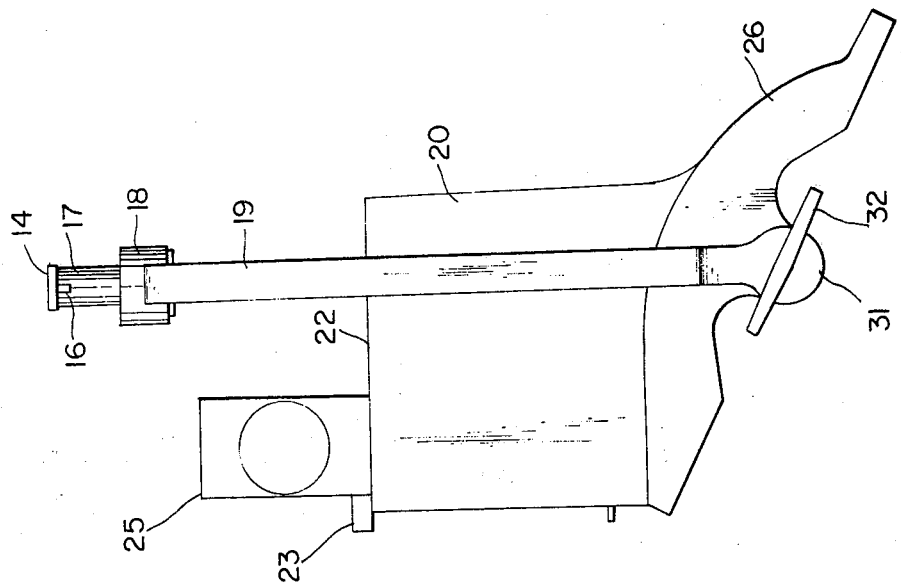
FIG. 3 is a side view of the assembly of FIG. 1 according to the invention.
Figure 2:
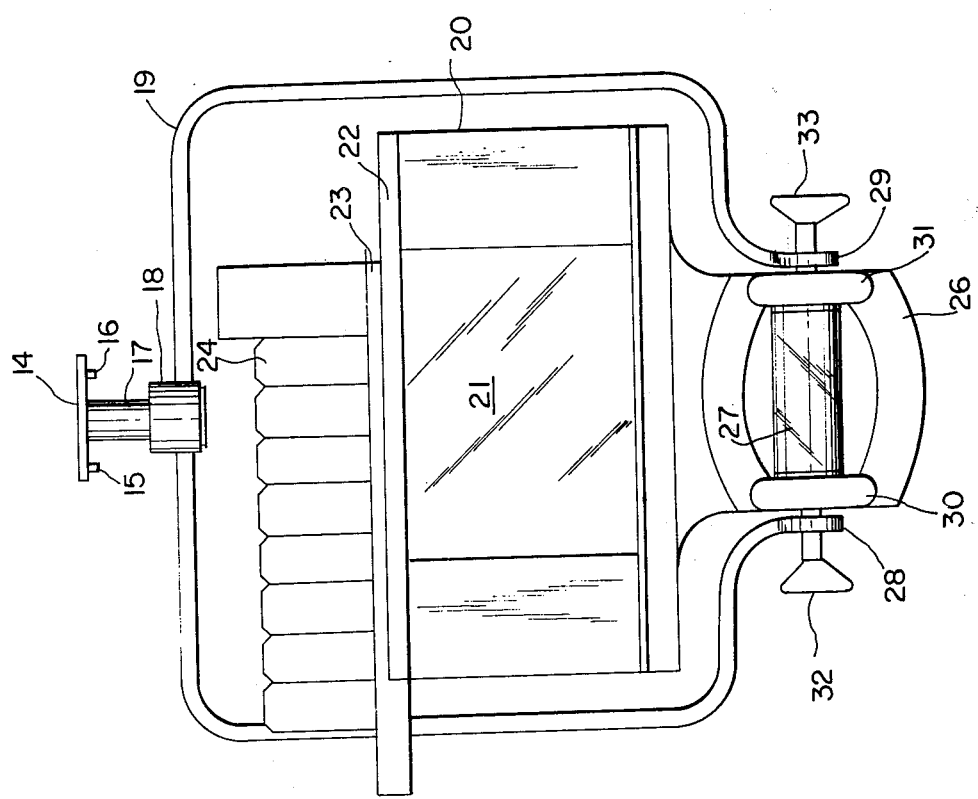
FIG. 2 is a frontal view of the assembly of FIG. 1 according to the invention.

A reflector and corresponding light device is securely mounted beneath housing 20 as shown in FIGS. 1 through 3. This device includes reflector 26 having a curvilinear surface comprising a material having light reflective characteristics as conventionally known in the art. A reflector light 27 is positioned in front of reflector 26 such that the light therefrom is reflected by reflector 26 to the area of the patient's mouth under operation which is desired to be illuminated by the dentist or dental assistant.

The reflector device described will provide for example a lighted area 3 inches in height having a longitudinal dimension of approximately 15 inches. This may be varied depending upon the positioning of the reflector device.

The reflector assembly is supported by yoke 19 and is positioned directly below housing 20, with the reflector element 26 being securely mounted to the base or bottom portion of housing 20. The end portions 28 and 29 of yoke 19 include mounting means 30 and 31 respectively including socket means for receiving reflector lamp 27. Handle means 32 and 33 (See FIG. 3) are also mounted to ends 28 and 29 respectively of yoke 19, for manual manipulation and positioning of the assembly 10 by the dentist or dental assistant, selectively to enable viewing by the patient. The assembly 10 is movable with respect to the handle means to enable variation in the angle of the display screen 21 to optimize the viewing angle for different patients. Appropriate power connections to power the reflector light and the projection unit is provided with the corresponding electrical connection being made for example from the interior of housing 20 through yoke 19 through support means 17. Alternatively, the unit may be self contained and battery powered with the appropriate battery means located within housing 20. Control means 37 may be mounted to the chair to enable the patient to control the volume of the audio signal or these may alternatively be included on a table next to the chair. Control means shown by knobs 38 and 39 are also included on the unit inself, in order that the dentist or dental assistant may control the audio and visual signals.

In operation, after the patient is seated in chair 12, the patient may select whatever film, video card or tape he desires to view. The dentist or dental assistant then moves the assembly 10 to proper position with respect to patient 12, and in this position the patient may view screen 21 upon which the selected program is displayed, and simultaneously the reflector device will illuminate the area of the patient's mouth upon which the dentist or dental assistant is operating. The patient may also view display screen 21 upon which the selected program is displayed without the reflector device being illuminated, if this is desired. The earphones 35, when not in use, are mounted on hook means 36 located above the dental chair 13. When in use, the dentist or dental assistant removes earphones 35 from storage location on hook 36 for use by the patient 12. The earphones through appropriate electrical connections conventional in the art and therefore not detailed herein, enables the patient to listen to the soundtrack of the selected program.

The reflector device including reflector 26 and reflector light 27 is positioned at the base of housing 20 such that the reflected light from reflector 26 lights or illuminates the patient's mouth or the area upon which the dentist or dental assistant is operating without interfering with the patient's view of the screen 21. Thus, the reflected light illuminates the area of the patient's mouth being operated upon, but does not reflect light into the patient's eyes and therefore does not interfere with the patient's viewing of the film being displayed on display screen 21. The visual and audio signals supplied to the patient have an analgesic effect. The yoke 19 is not only movable within track 11, but also may be swivelled to any desired location through swivel mounting means 18.

We claim:

1. An assembly to illuminate the area of a dental patient's mouth under operation and provide a display screen for viewing by the patient comprising:
   a housing having a display screen to display images,
   yoke means to support and variably position the housing in front of the patient,
   track means, the housing being movably supported in the track means by support means coupled to the yoke means, the support means enabling the housing to be laterally translated and including swivel means to enable the housing and light reflector assembly to be simultaneously swivelled,
   a light reflector assembly mounted below the housing having a reflector and light, the reflector being securely mounted to the bottom portion of the housing, said yoke means supporting the light enabling the reflector to illuminate the area of the patient's mouth under operation without interfering with the patient's view of the display screen, and
   earphones for use by the patient to reproduce the soundtrack of the selected program on the display screen.

2. The assembly recited in Claim 1 further comprising projection means contained within the housing to display a selected program onto the display screen.

3. The assembly recited in Claim 2 further comprising playback means mounted to the housing to play back a selected program to the projection means for display on the display screen.

* * * * *